(12) United States Patent
Andelic et al.

(10) Patent No.: US 9,651,479 B2
(45) Date of Patent: May 16, 2017

(54) METHOD AND ANALYZER FOR DETERMINING A MEASURED VALUE OF A MEASURED VARIABLE OF PROCESS AUTOMATION TECHNOLOGY

(71) Applicant: Endress + Hauser Conducta Gesellschaft für Mess- und Regeltechnik mbH + Co. KG, Gerlingen (DE)

(72) Inventors: Edin Andelic, Hagen (DE); Ralf Bernhard, Stuttgart (DE); Michael Littmann, Beitigheim-Bissingen (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 121 days.

(21) Appl. No.: 14/680,574

(22) Filed: Apr. 7, 2015

(65) Prior Publication Data

US 2015/0285736 A1    Oct. 8, 2015

(30) Foreign Application Priority Data

Apr. 8, 2014  (DE) .................. 10 2014 104 947

(51) Int. Cl.
| | | |
|---|---|---|
| *G01N 21/31* | (2006.01) | |
| *G01N 21/63* | (2006.01) | |
| *G01N 21/78* | (2006.01) | |
| *G01N 33/00* | (2006.01) | |
| *G01N 21/27* | (2006.01) | |

(52) U.S. Cl.
CPC ........... *G01N 21/31* (2013.01); *G01N 21/274* (2013.01); *G01N 21/314* (2013.01); *G01N 21/63* (2013.01); *G01N 21/78* (2013.01); *G01N 21/783* (2013.01); *G01N 33/0036* (2013.01); *G01N 2201/062* (2013.01); *G01N 2201/129* (2013.01);
(Continued)

(58) Field of Classification Search
CPC .... G01N 21/274; G01N 21/31; G01N 21/314; G01N 21/63; G01N 21/78; G01N 21/783; G01N 2201/062; G01N 2201/129; G01N 33/0036; Y10T 436/16; Y10T 436/173076; Y10T 436/173845
USPC .................. 436/43, 103, 110, 111, 164, 165; 422/82.05, 82.09, 83; 702/22, 24, 25
See application file for complete search history.

(56) References Cited

U.S. PATENT DOCUMENTS

| | | | |
|---|---|---|---|
| 5,550,053 A * | 8/1996 | Salpeter ............... | G01N 21/274 250/252.1 |
| 2012/0258542 A1* | 10/2012 | Kathe .................... | G01N 21/78 436/43 |

(Continued)

*Primary Examiner* — Maureen Wallenhorst
(74) *Attorney, Agent, or Firm* — Christopher R. Powers; PatServe (57) ABSTRACT

A method and analyzer for determining a measured value of a measured variable of process automation technology in a liquid or gaseous medium by means of an optical sensor includes taking a sample of the medium; mixing the sample with one or more reagents; supplying an emitter of the optical sensor with an exciter signal for producing sent light, wherein the sent light by interaction with the mixed sample is converted into received light as a function of the measured variable; producing a receiver signal by means of a receiver of the optical sensor from the converted, received light; and determining the measured value based on the receiver signal and a calibration function, which includes a term which takes aging of the reagents into consideration.

14 Claims, 8 Drawing Sheets

(52) U.S. Cl.
CPC .... *Y10T 436/16* (2015.01); *Y10T 436/173076* (2015.01); *Y10T 436/173845* (2015.01)

(56) References Cited

U.S. PATENT DOCUMENTS

2012/0285224 A1* 11/2012 Zachmann ......... G01N 35/1097
  73/64.56
2013/0265568 A1* 10/2013 Micheels ............ G01N 21/359
  356/51

* cited by examiner

METHOD AND ANALYZER FOR DETERMINING A MEASURED VALUE OF A MEASURED VARIABLE OF PROCESS AUTOMATION TECHNOLOGY

TECHNICAL FIELD

The invention relates to a method for determining a measured value of a measured variable of process automation technology in a liquid or gaseous medium by means of an optical sensor. The invention relates further to an analyzer for determining a measured value of a measured variable, especially for analyzing for at least one ion concentration, especially an ammonium concentration.

BACKGROUND DISCUSSION

The terminology "analyzer" in the sense of this invention means a measuring apparatus of process automation technology, which measures with a wet chemical method certain concentrations of substances, for example, an ion concentration in a medium to be analyzed. For this, a sample is removed from the medium to be analyzed. Most often, the sample is removed fully automatically by the analyzer, for instance, by pumps, hoses, valves, etc. For determining the concentration of a substance of a certain species, reagents specially developed for the respective concentration of substance and stored availably in the analyzer housing are mixed with the sample to be measured. A color reaction of this mixture caused thereby is then measured by means of a suitable measuring device, for example, by means of a photometer. More exactly stated, sample and reagents are mixed in a cuvette and measured with different wavelengths using the sent light method. Based on the light absorption and a furnished calibration model, the measured value is, in this way, ascertained on the receiving side.

Figure 1:
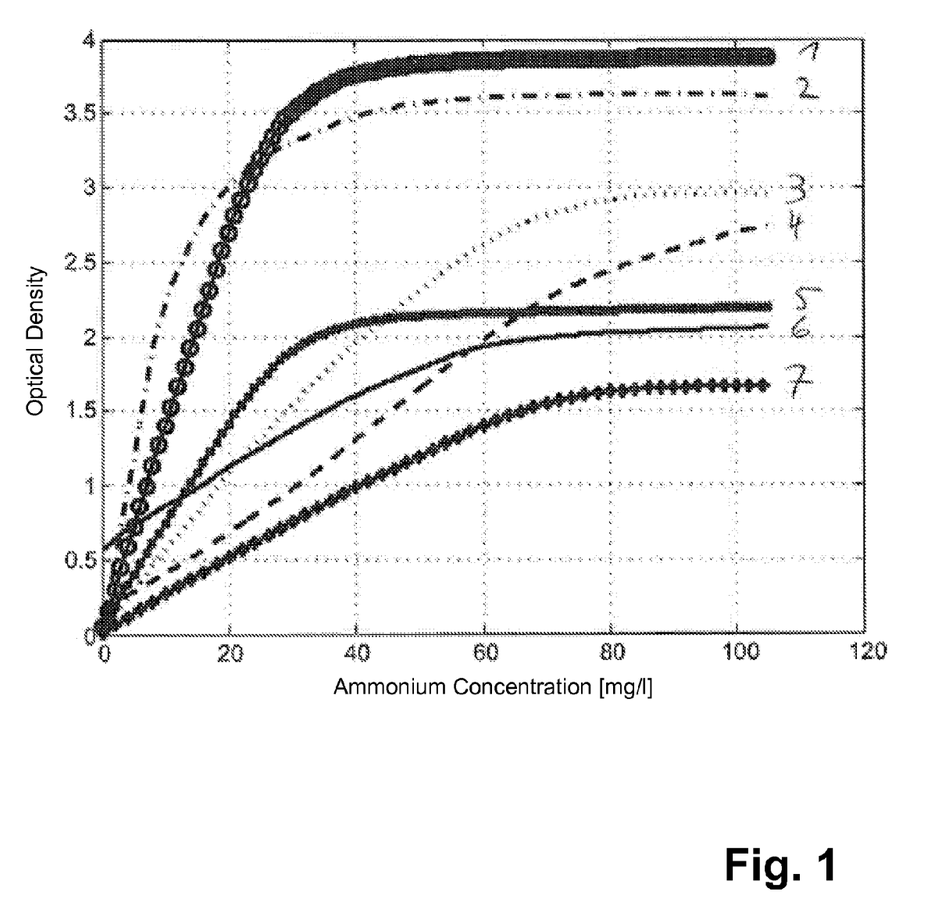
FIG. 1 a graph of absorbed light as a function of the concentration of a substance.

In designing a corresponding calibration model, the following difficulties result: The relationship between absorption and concentration of the substance is not linear and is influenced by external disturbance variables. FIG. 1 shows a typical graph of absorbed light as a function of the concentration of a substance, here, by way of example, ammonium, for seven different wavelengths 1-7. It is to be seen that the curves are not linear, above all, at the higher concentrations of the substance. Users additionally desire that the analyzer be able to operate as long as possible self-sufficiently, i.e. without (re-) calibrating and (re-) adjusting or replacement of reagents.

SUMMARY OF THE INVENTION

An object of the invention is to provide a calibration model, which shows the relationship between absorption and concentration of substance as exactly as possible and is simultaneously robust against disturbing influences.

The object is achieved by a method comprising the steps as follows: taking a sample of the medium; mixing the sample with one or more reagents; supplying an emitter with an exciter signal for producing sent light, wherein the sent light by interaction with, especially by absorption by, the mixed sample is converted into received light as a function of the measured variable; producing a receiver signal by means of the receiver from the converted, received light; and determining the measured value based on the receiver signal and a calibration function. The method is characterized in that, in determining the measured value, aging of the reagents is taken into consideration, especially the calibration function includes a term which takes aging of the reagents into consideration. One of the main causes for why a measured value can deviate from the true measured value has been found to be the aging of the reagents. Frequently, also, newer reagents are mixed with older reagents, so that an exact determining of the age of the reagents is not possible. The method of the invention provides that also in the case of older reagents the measured value can be correctly determined. A readjusting of the analyzer is not necessary.

Figure 2A:
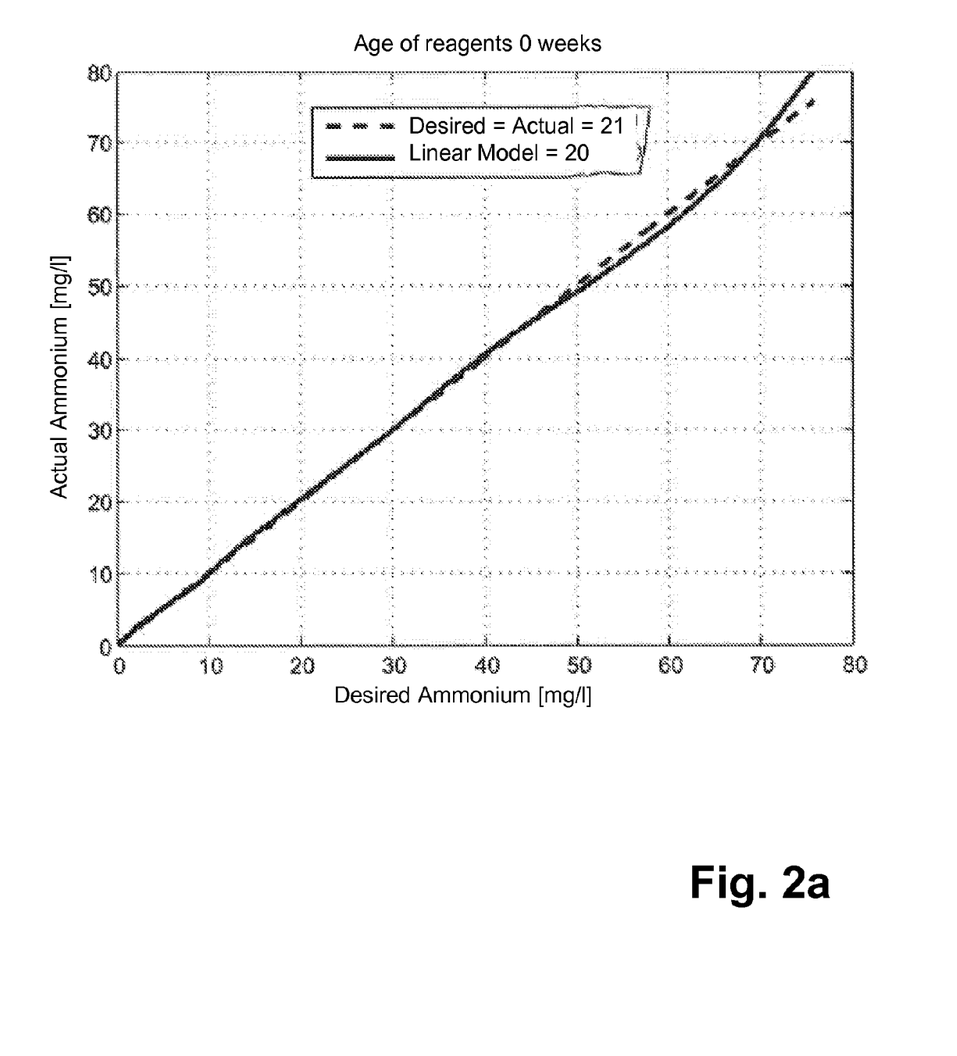
FIG. 2a-2c linear interpolation between determined points.
Figure 2B:
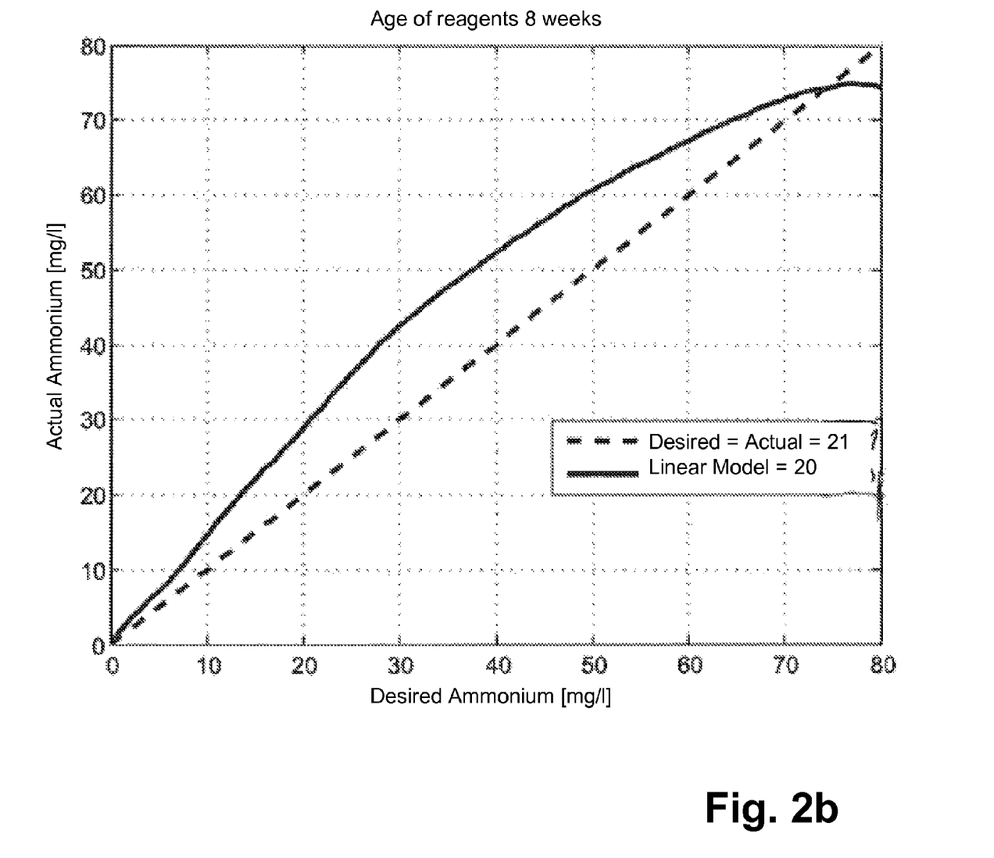
Figure 2C:
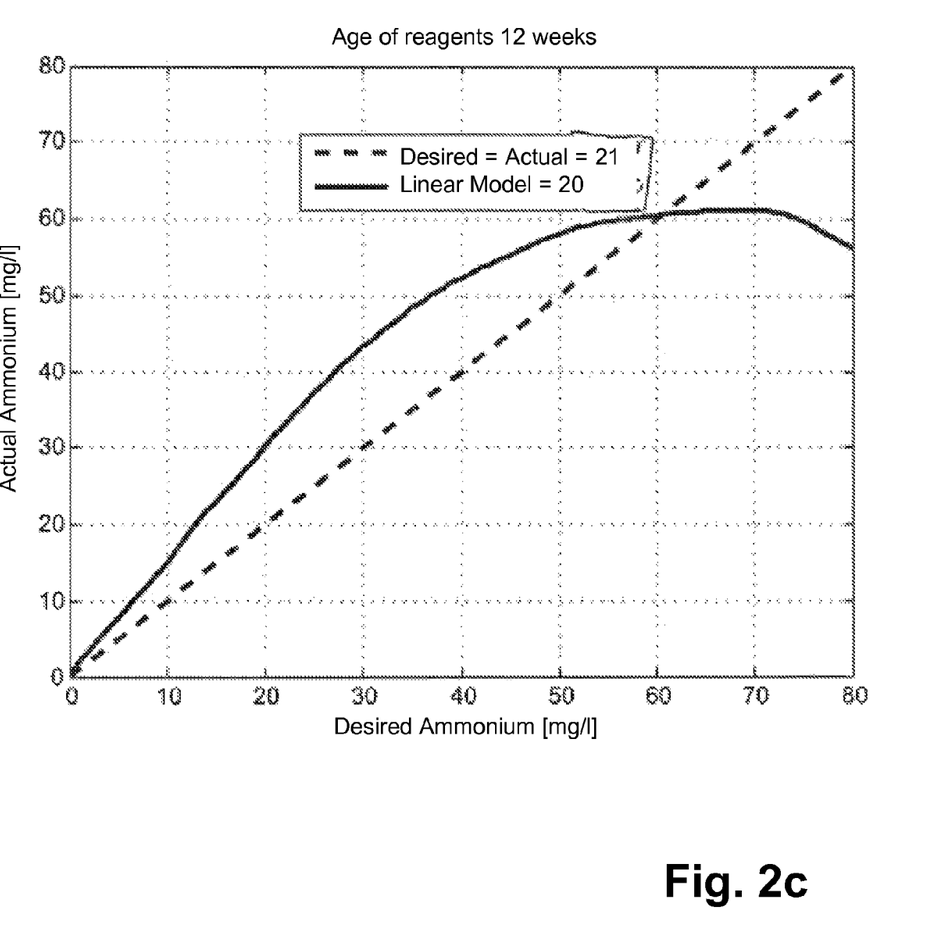

In FIGS. 2a-2c, a simple calibration model was selected. More exactly stated piecewise linear interpolation between determined points was used as a calibration model and stored in a table. FIG. 2a shows the linear interpolation model in the case of fresh reagents, FIG. 2b in the case of 8 week old reagents and FIG. 2c in the case of 12 week old reagents. Shown are concentrations, which the linear calibration model predicts as well as the true ammonium concentrations. Measurements were made in 1 mg/l steps. The concentrations were predetermined by a so-called sample supplier, such being a programmable device, which fully automatically samples, respectively mixes, a predetermined ammonium concentration of any size. These samples are then pulled by vacuum to an analyzer, into a cuvette therein, and measured. The true measured value is indicated with the reference character 21 and the measured value of the interpolation in a table is labeled with the reference character 20. One can see that with increasing reagent age the accuracy of the model over the total measuring range clearly decreases. In fact, in the case of older reagents, beyond a certain concentration of substance, the model becomes completely insensitive.

In an advantageous embodiment, the calibration function is created by means of a kernel method.

Preferably, the kernel method is a support vector machine or a kernel Fisher discriminant. These two methods make it possible to express the calibration function such that aging of the reagents is taken into consideration.

In an advantageous form of embodiment, the measured value c(x) is calculated by $$c(x) = a_0 + \Sigma_{i=1}^{N} a_i \cdot k(x, x_i),$$

wherein the kernel function $$k(x, x_i) = \exp(-\mu \|x_i - x\|^2),$$

wherein x is a data vector comprising the receiver signal of the at least two wavelengths, $x_i$ are support vectors, $a_0$, $a_i$ are coefficients, $\mu$ is a kernel parameter, and N is the number of support vectors in the form of a natural number, especially between 50 and 300.

The data vector includes at least one of the parameters, ambient temperature of the analyzer, temperature in the analyzer, sampling point in time, process duration, reagents, reagent age, and/or mixing ratios of reagents. These parameters influence the calibration function and can also be taken into consideration by application of a kernel method for determining the same.

In an advantageous form of embodiment, the support vectors, coefficients and kernel parameters are determined earlier.

Preferably, the reagents are not replaced for at least 10 weeks, especially 12 weeks. This saves the user costs and time.

In a preferred embodiment, the method is executed in an analyzer for analyzing for at least one ion concentration, especially ammonium concentration.

The object is further achieved by an analyzer, wherein the analyzer is embodied for performing an above described method.

In an advantageous form of embodiment, the analyzer includes a superordinated unit, especially a transmitter, wherein the superordinated unit executes the above described method.

Preferably, the superordinated unit calculates the kernel function and the measured value.

BRIEF DESCRIPTION OF THE DRAWINGS

The invention will now be explained in greater detail based on the drawings, the figures of which show as follows.

DETAILED DISCUSSION IN CONJUNCTION WITH THE DRAWINGS

Figure 3:
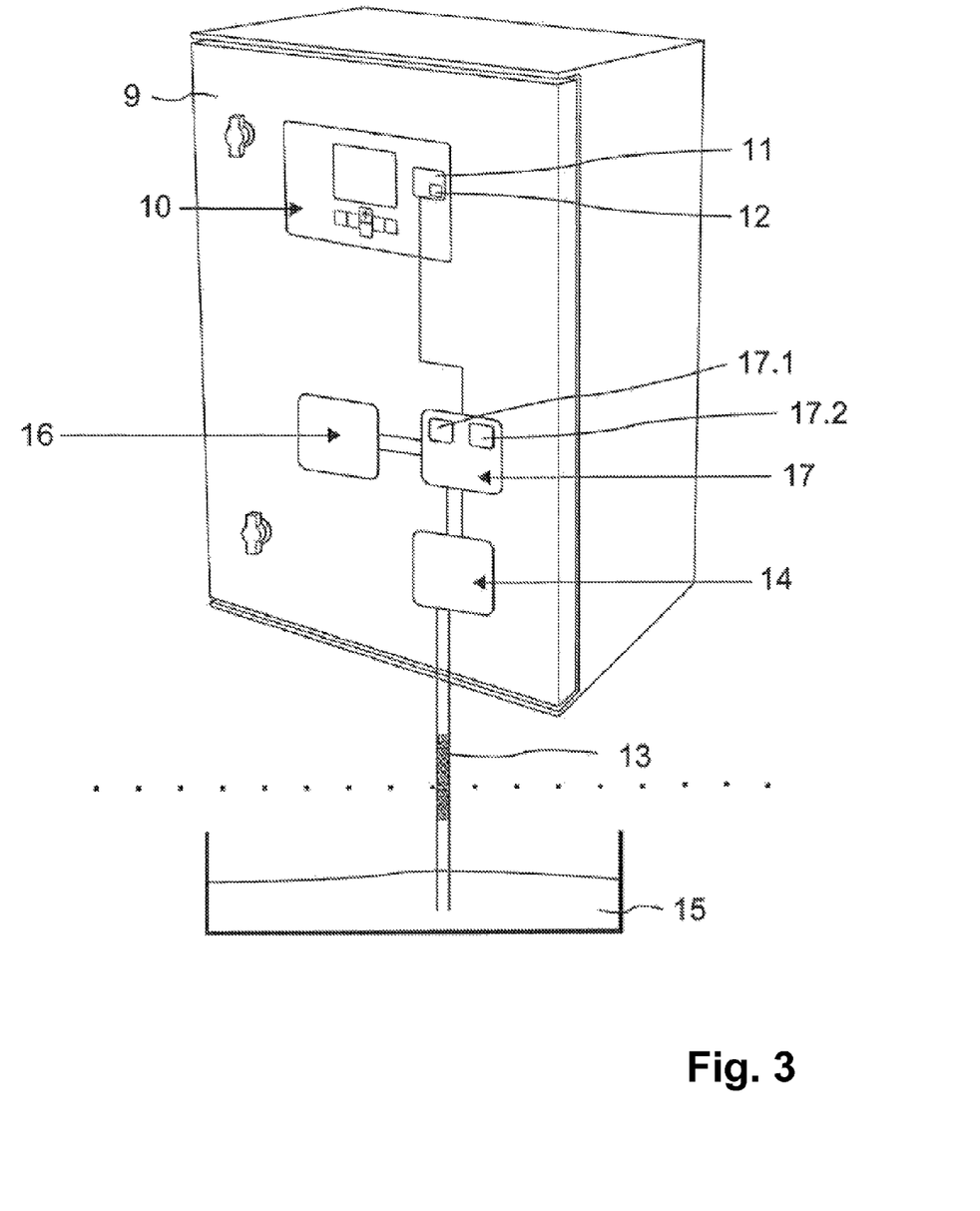
FIG. 3 the analyzer of the invention.

The method of the invention is applied in an analyzer 9, which will be described first.

An analyzer 9 measures with wet chemical methods certain concentrations of substances, for example, an ion concentration in a medium to be analyzed. For example, an analyzer of the invention 9 measures the ammonium concentration. Other examples of measured ions include, for instance, phosphate, nitrate, etc.

Taken for such purpose from a medium 15 to be analyzed is a sample 13. Most often, the sample 13 is taken fully automatically by the analyzer, for instance, by subsystems 14, such as pumps, hoses, valves, etc. For determining the concentration of a substance of a certain species, reagents 16 specially developed for the respective concentration of substance and stored availably in the analyzer housing are mixed with the sample 13 to be measured. This is shown symbolically in FIG. 3. Actually, a number of containments with different reagents are provided and the reagents removed via the mentioned pumps, hoses, valves, etc. and, in given cases, mixed. Also separate pumps, hoses, valves can be used for each procedure (taking the sample, mixing of reagents, etc.).

A resulting color reaction of this mixture is then measured by means of a suitable measuring device, for example, by means of a photometer 17. In this regard, for example, the sample 13 and the reagents 16 are mixed in a cuvette and measured optically with at least two different wavelengths using the sent light method. Thus, light of at least two wavelengths 1-7 is sent by means of a light emitter 17.1 through the sample 13. Associated with the emitter 17.1 is a receiver 17.2 for receiving the sent light. Based on the light absorption and a furnished calibration function, then, receiving side, the measured value is produced. The emitter 17.1 comprises, for example, one or more LEDs, i.e. one LED per wavelength, or a corresponding light source with broadband excitation. The receiver 17.2 can comprise, for instance, one or more photodiodes.

The analyzer 9 further includes a transmitter 10 with a microcontroller 11 including memory 12. Via the transmitter 10, the analyzer 9 can be connected to a fieldbus. Additionally, the analyzer 9 is controlled via the transmitter 10. Thus, for example, the taking of a sample 13 from the medium 15 is initiated by the microcontroller 11 by corresponding control commands provided to the subsystems 14. Also, the measuring by the photometer 17 is controlled by means of the microcontroller.

According to the method of the invention, in determining the measured value by means of light absorption and the calibration function, aging of the reagents is taken into consideration. It is especially a feature of the invention that the compensation of aging happens not by means of an individual, separate, mathematical term, but, instead, aging compensation is present in all coefficients of the calibration model.

The absorptions by the individual wavelengths 1-7 are considered together in the form of a vector variable, the data vector x, which here contains the individual absorptions as entries. There are, however, in this regard, certainly other characteristics possible, in which case the vector x also includes measured variables such as one of the parameters, ambient temperature of the analyzer, temperature in the analyzer, sampling point in time, process duration, reagents, and/or mixing ratios of reagents. Frequently, it happens that newer reagents are mixed with older reagents, so that an exact determining of age is not possible. In many applications, it is desired that the reagents not be replaced for at least 10 weeks, especially 12 weeks, and that no adjusting of the analyzer occur.

Figure 4A:
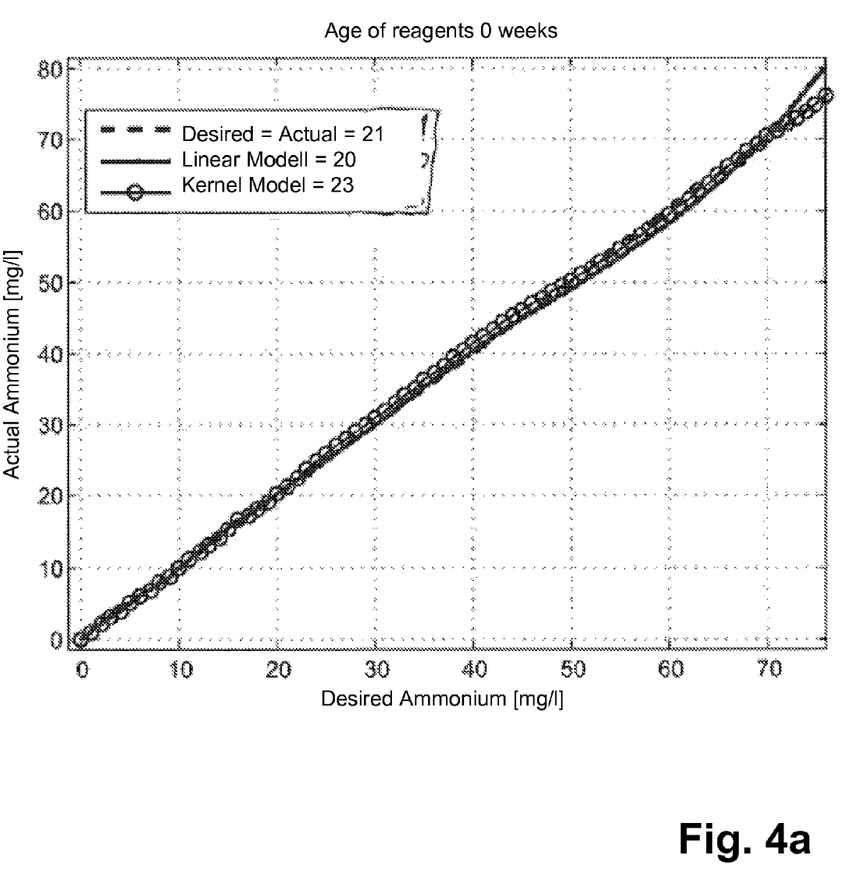
FIGS. 4a-4c substance concentrations ascertained with the method of the invention.
Figure 4B:
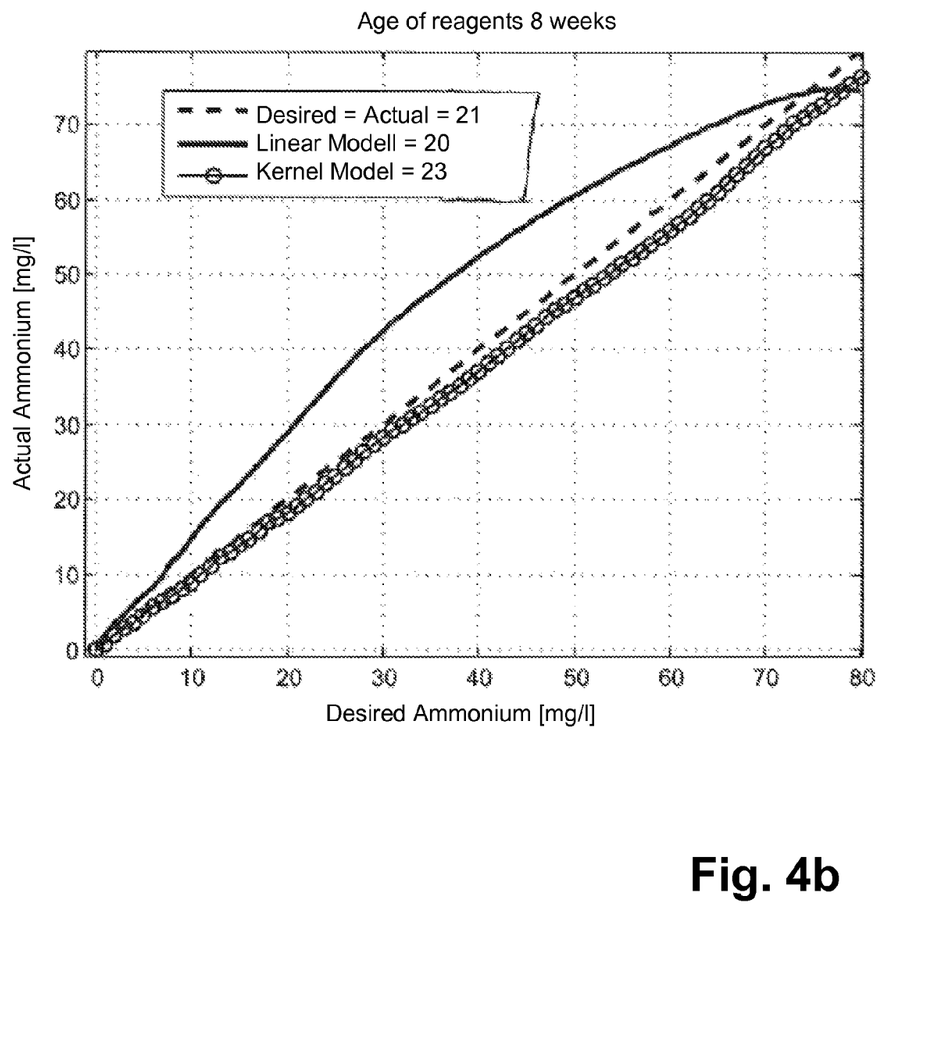
Figure 4C:
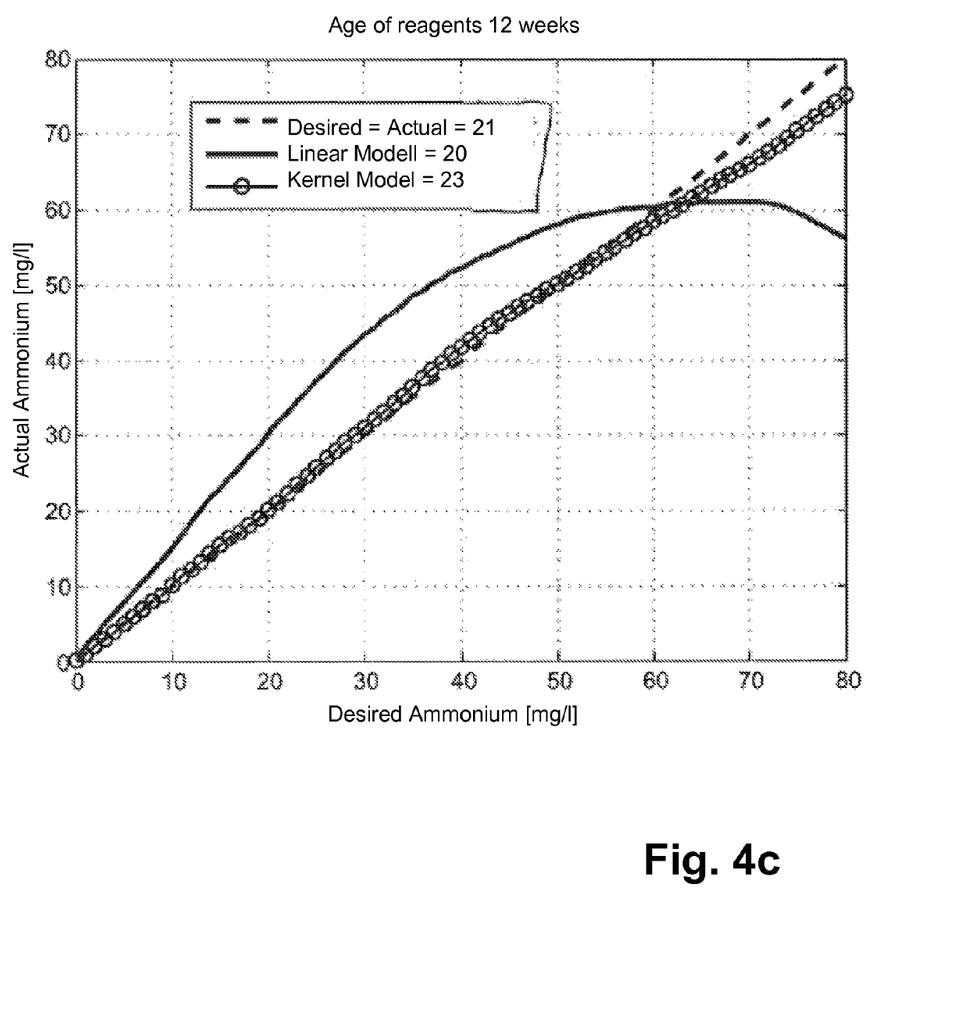

For taking aging of the reagents into consideration, the calibration function is created by means of a kernel method. FIGS. 4a-c show that with kernel methods, in spite of increasing reagent age, more exact measured values can be made than with a simple linear interpolation 20 such as shown in FIGS. 2a-c. Examples of such kernel methods include the support vector machine (SVM) and the kernel Fisher discriminant (KFD) 23. For reasons of perspicuity, the figures show only the KFD method.

The greater calculational effort and memory necessary for the methods can be tolerated, since, such as in the case of the analyzer 9 described here, frequently a measured value is produced only every 10 minutes.

In the following, the basic principles of kernel methods will be explained briefly.

In kernel methods, data (in this case the data vector x with absorptions for different wavelengths) are transformed by a non-linear, multidimensional mapping, wherein the data are approximateable linearly in the new space. This multidimensional mapping does not need to be explicitly calculated. Functions, which fulfill a certain condition, do this implicitly, in that they calculate the scalar product of two transformed vectors. In the literature, this is referred to as the "kernel trick"—in this context, such functions are referred to as kernel functions.

All algorithms, which are presentable by scaler products of the data vectors, are transferable by such kernel functions into a non-linear version. Known representatives of such algorithms are the support vector machine (SVM) and the kernel Fisher discriminant (KFD) 23.

The so trained model then appears as follows: a concentration of substance c(x), e.g. an ammonium concentration, is associated with the new data vector x according to the formula $$c(x) = a_0 + \Sigma_{i=1}^{N} a_i \cdot k(x, x_i),$$

wherein the kernel function $$k(x, x_i) = \exp(-\mu \|x_i - x\|^2),$$

with $x_i$ as support vectors, $a_0$, $a_i$ as coefficients, $\mu$ as a kernel parameter, and N as the number of support vectors in the form of a natural number, especially between 50 and 300, wherein this can also be larger or smaller.

The support vectors $x_i$, coefficients $a_0$ and $a_i$, and kernel parameter p usable for the analyzer 9 are earlier determined, e.g. in the laboratory under laboratory conditions, i.e. at a certain, controlled temperature, humidity, air pressure, etc.

The coefficients $a_0$ and $a_i$ are determined in the training of the kernel method. In the SVM, for instance "training" means, from a mathematical point of view, the solution of a quadratic, optimizing problem. In KFD, training occurs by solving a regularized least squares problem. KFD is equivalent to the so-called "kernel ridge regression". Further explanations are available to those skilled in the art in the literature.

The kernel parameter p is determined in such a manner that a training data set is divided into M equally large parts, wherein M is a natural number. Then M−1 parts are used for training. The kernel parameter is varied within a certain value range until the trained model produces the smallest error on the omitted, "foreign" data packet. The is repeated M-times with, in each case, a different omitted data packet. Finally, that kernel parameter is selected, which on average has produced the least error. This procedure is called "cross validation".

The method of the invention is executed by the analyzer 9. As already mentioned, the analyzer 9 includes a transmitter 10, wherein the claimed method is executed by the transmitter 10.

The support vectors, coefficients and kernel parameter are furnished fixed in the firmware of the transmitter 10.

The invention claimed is:

1. A method for determining a measured value of a measured variable of process automation technology comprising:
    taking a sample of a liquid or gaseous medium;
    mixing the sample with one or more reagents to generate a mixed sample;
    supplying an emitter of an optical sensor with an exciter signal to produce sent light, the emitter structured to produce sent light of at least two wavelengths, and the optical sensor including a receiver associated with the emitter and structured to receive received light, wherein the sent light is converted into received light as a function of the measured variable by absorption by the mixed sample;
    producing a receiver signal by means of the receiver from the received light; and
    determining the measured value based on the receiver signal and a calibration function, wherein the calibration function includes a term based on a predetermined model of the aging of the reagents such that the measured value is determined based at least partially on the age of the reagents.

2. The method as claimed in claim 1, wherein the calibration function is generated by means of a kernel method.

3. The method as claimed in claim 2, wherein the kernel method is a support vector machine or a kernel Fisher discriminant.

4. The method as claimed in claim 3, wherein the measured value is calculated by $$c(x)=a_0+\Sigma_{i-1}^{N}a_i \cdot k(x,x_i),$$

with a kernel function $$k(x,x_i)=\exp(-\mu\|x_i-x\|^2),$$

wherein x is a data vector comprising the receiver signal of the at least two wavelengths, $x_i$ are support vectors, $a_o$, $a_i$ are coefficients, $\mu$ is a kernel parameter, and N is a number of support vectors in the form of a natural number.

5. The method as claimed in claim 4, wherein the data vector x further includes at least one of the parameters, ambient temperature of a analyzer, temperature in the analyzer, sampling point in time, process duration, reagents, reagent age, and/or mixing ratios of reagents.

6. The method as claimed in claim 4, wherein the support vectors $x_i$, coefficients $a_o$, $a_i$ and kernel parameter $\mu$ are determined before the measured value is determined.

7. The method as claimed in claim 1, wherein the reagents are not replaced for at least 10 weeks.

8. The method as claimed in claim 1, wherein the method is executed in an analyzer for analyzing for at least one ion concentration.

9. The method as claimed in claim 1, wherein coefficients and parameters of the calibration function are at least partially based on the aging of the reagents.

10. An analyzer for determining a measured value of a measured variable of a sample, the analyzer comprising:
    a mixing cell structured to enable mixing of a sample with one or more reagents to produce a mixed sample;
    a measuring device including an emitter structured to emit sent light of at least two wavelengths and a receiver associated with the emitter for receiving received light, wherein the sent light is converted into received light as a function of a measured variable by absorption by the mixed sample, and wherein the receiver generates a receiver signal from the received light; and
    a controller configured to determine a measured value of the mixed sample based on the receiver signal and a calibration function, wherein the calibration function includes a term based on a predetermined model of the aging of the reagents such that the measured value is determined based at least partially on the age of the reagents.

11. The analyzer as claimed in claim 10, wherein the calibration function is generated by means of a kernel method.

12. The analyzer as claimed in claim 11, wherein the measured value is calculated by $$c(x)=a_0+\Sigma_{i-1}^{N}a_i \cdot k(x,x_i),$$

with a kernel function $$k(x,x_i)=\exp(-\mu\|x_i-x\|^2),$$

wherein x is a data vector comprising the receiver signal of the at least two wavelengths, $x_i$ are support vectors, $a_o$, $a_i$ are coefficients, $\mu$ is a kernel parameter, and N is a number of support vectors in the form of a natural number.

13. The analyzer as claimed in claim 12, wherein the coefficients and parameters of the calibration function are at least partially based on the aging of the reagents.

14. The analyzer as claimed in claim 10, wherein the controller is a transmitter.

* * * * *